United States Patent [19]

Altschuler et al.

[11] Patent Number: 4,872,122
[45] Date of Patent: Oct. 3, 1989

[54] INTERACTIVE STATISTICAL SYSTEM AND METHOD FOR PREDICTING EXPERT DECISIONS

[75] Inventors: Martin D. Altschuler, Wallingford; Richard Whittington, Media, both of Pa.

[73] Assignee: University of Pennsylvania, Philadelphia, Pa.

[21] Appl. No.: 65,304

[22] Filed: Jun. 19, 1987

[51] Int. Cl.$^4$ .......................... G06F 15/42; G06F 9/00
[52] U.S. Cl. ..................................... 364/554; 364/300; 364/275.7; 364/413.02; 364/513
[58] Field of Search ............... 364/300, 513, 415, 554, 364/413.02, 200

[56] References Cited

U.S. PATENT DOCUMENTS

| 4,595,982 | 6/1986 | Burt | 364/300 |
|---|---|---|---|
| 4,648,044 | 3/1987 | Hardy et al. | 364/513 |
| 4,658,370 | 4/1987 | Erman et al. | 364/300 |
| 4,675,829 | 6/1987 | Clemenson | 364/513 |
| 4,730,259 | 3/1988 | Gallant | 364/415 |
| 4,733,354 | 3/1988 | Potter et al. | 364/413.02 |

OTHER PUBLICATIONS

N.E. Jour. Med, Jan. 29, 1987; "Medical Progress: Decision Analysis"; S. G. Pauker et al.; pp. 250–258.
Computer, Sep. 1984; "Knowledge-Based Expert System: A tutorial"; F. Hayes-Roth; pp. 11–28.
Annals Inter. Med, Dec. 1985 (V103, #6); "Treatment Advice of a Computer-Based Cancer Chemotherapy Protocol"; D. H. Hickam et al; pp. 928–936.
Jour. Nuclear Med. Tech., Sep. 1986 (V14, #3); "Expert Systems: Applications of A.I. in Medicine"; J. A. Siegel et al.; pp. 175–181.
IEEE Workshop on Principles of Knowledge-Based Systems, Dec. 1984; "Learning of Expert Systems from Data"; P. Cheeseman; pp. 115–121.
Annals Inter. Med, Feb. 1987 (V106, #2); "Decision Analysis: A progress Report"; J. P. Kassirer et al.; pp. 275–290.
Jour. AMA, Jul. 3, 1987 (V258, #1); "Computer Programs to Support Clinical Decision Making"; E. Shortliffe; pp. 61–66.
Jour. AMA, Jul. 3, 1987 (V258, #1); "DXplain: An Evolving Diagnostic Decision-Support System"; G. O. Barnett et al.; pp. 67–74.
"Clinical Decision Analysis: An Annotated Bibliography"; C. iefe; pp. 1–21.
IEEE Tran on Systems, Man, & Cybernetics, Mar.-/Apr. 1987 (V17, #2).
"A Probabilistic Causal Model For Diagnostic Problem Solving-Part I: Integrating Symbolic Causal Inference with Numeric Probabilistic Inference"; Y. Peng et al.; pp. 146–162.

Primary Examiner—Parshotam S. Lall
Assistant Examiner—Kevin J. Teska
Attorney, Agent, or Firm—Ratner & Prestia

[57] ABSTRACT

A system and method for selecting from a set of output actions for combinatory situations such as medical diagnosis defined by a plurality of input parameters. A decision making structure is established by an expert having a plurality of linked nodes. Random values of the input parameters are generated, which includes biasing the random values by a function of a preceding response. The steps are repeated until a sufficient number of responses having a predetermined statistical significance is achieved for each node. After this set up and teaching, the accuracy of the system's predictions may be verified against actual responses by the expert. The decision making structure may be interrogated by entering a situation to be analyzed. The path the expert would take through the decision making structure is predicted by determining the probability of the expert's response at each node in the structure to arrive at an output action. A plurality of structures may be established, one for each individual expert, allowing interrogation of any or all of the decision making structures.

18 Claims, 12 Drawing Sheets

INTERACTIVE STATISTICAL SYSTEM AND METHOD FOR PREDICTING EXPERT DECISIONS

FIELD OF THE INVENTION

This invention relates to expert systems and methods.

BACKGROUND OF THE INVENTION

In the past, many expert systems have been developed by establishing a set of rules which defined the individual's area of expertise. Such rule-based systems, however, have had difficulty in addressing the combinatory situations described by a plurality of input variables such as in the medical field. The reason being that a rule-based system needs to address specific circumstances and has been objectionable in areas where the possible combinations are too numerous.

Further, prior rule-based systems have required the expert to work along with a programmer or knowledge engineer in order to implement the system. This has proven to be a time-consuming and expensive process which involves the knowledge engineer translating the expert's decision making process into a fixed program. The amount of time necessary to develop and program a rule-based system, plus the structure of the program that must be written, make these systems difficult to amend in situations where the area of expertise is constantly changing, adapting or improving with new developments.

An additional limitation of the rule-based expert systems is the need for agreement in the particular field of expertise upon the preferred analysis and treatment of the problem in question. In a field such as medicine, for example, this agreement is usually lacking, with many recognized experts having different and sometimes conflicting opinions of the preferred method of analysis and treatment.

In a non-rule based system, Burt U.S. Pat. No. 4,595,982, teaches arranging an internal representation of the expert's logical process and characterizing the situation in terms of a series of intermediate judgments.

SUMMARY OF THE INVENTION

A system and method for selecting from a set of output actions for combinatory situations which are defined by a plurality of input parameters. In the set up and teaching operations, the expert first establishes a decision making structure having a plurality of linked nodes. Random values are then generated for the input parameters in which the operation of the random values is biased so as not to conflict with responses to preceding nodes. Random value generation and corresponding responses are then repeated until a sufficient number of responses are given to achieve a predetermined statistical significance for each node.

Further, in accordance with this invention, the decision making structure may be interrogated by first entering a situation to be analyzed. The system then predicts which path the expert will take through the decision making structure to arrive at an output action. The path is predicted by determining the probability of the expert's response at each node in the decision making structure.

A decision making structure may be established for each of a plurality of experts. The steps are individually repeated for each expert's decision making structure. The user may then have the option of selecting one or more of the expert's decision making structures to interrogate and then can compare the treatment selection of one expert with another.

DETAILED DESCRIPTION OF THE INVENTION

Figure 1A:
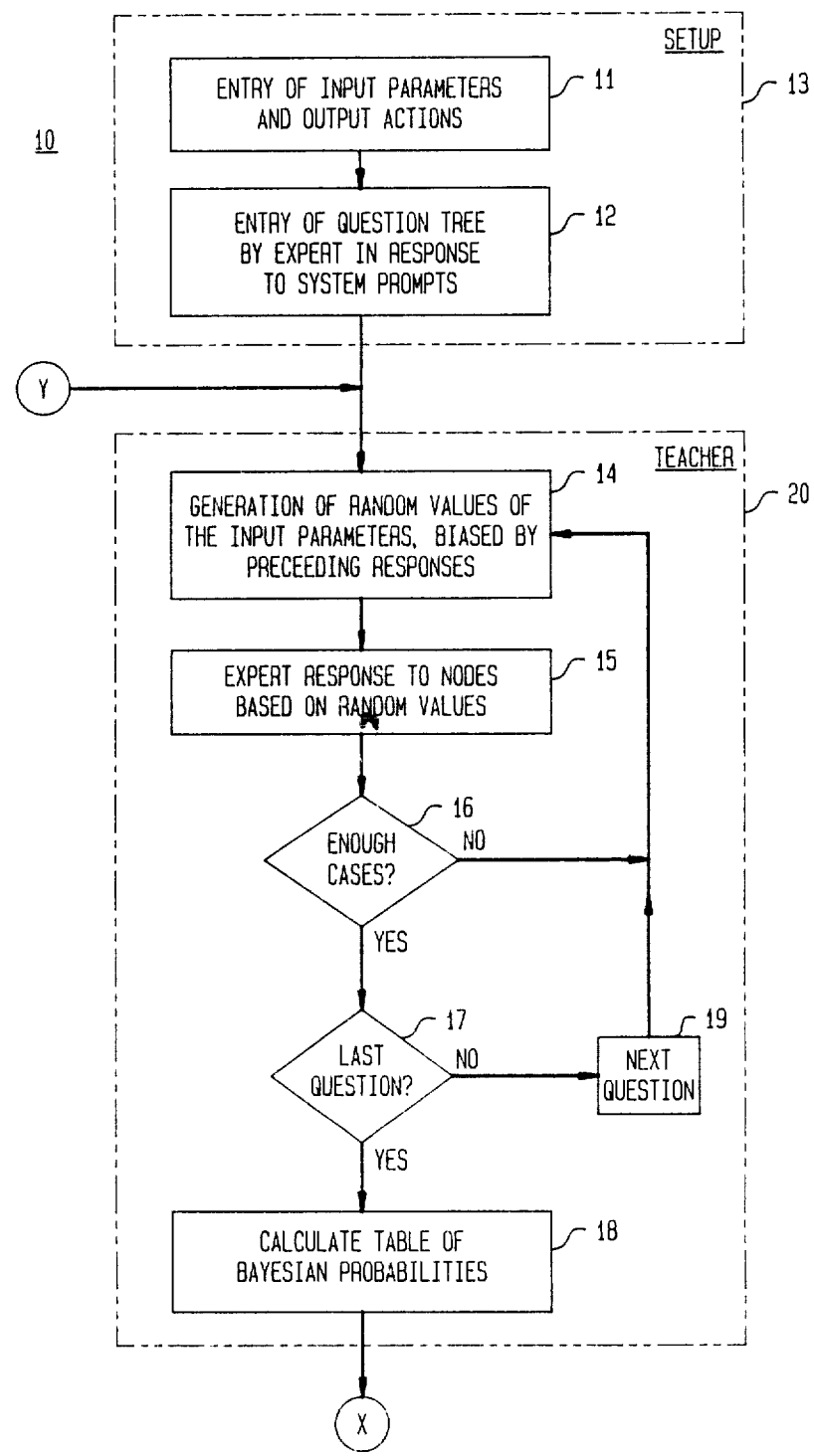
FIGS. 1A and 1B, taken together, are an overview of the set up, teacher, verifier and interrogator sections of the system of the present invention.

There is shown in FIGS. 1A, B an interactive statistical inference method and system 10 (hereinafter "system") by which users may obtain the judgment and decision making steps of a plurality of experts in a particular field of study without the expert's presence. The system is particularly adapted for selecting among a plurality of action options for combinatory situations described by a plurality of input parameters. Medicine is an example of a field of study for which the system is well suited. In examining a case of prostate cancer, for instance, there are 22 different parameters, (i.e. input variables) that a physician may look at before deciding on the patient's treatment (output action). The possible combinations of these 22 vraiables (shown in Appendex B available within the application file wrapper) yield approximately 54 billion different cases. By first applying the well known chi square statistical analysis to determine which variables are significant at each decision making step and then the conventional Bayesian statistical analysis to determine the probability that the expert which taught the system would choose a particular output action, the system is able to determine, based upon the expert physician's own experiences, the probability of the expert physician selecting a given treatment.

The system application program is a software shell to create, teach, verify and maintain expert systems with the use of statistical data derived from simulated case situations. It consists of five main parts: (1) set up 13, (2) teacher 20, (3) modifier (editor), (4) verifier 25, and (5) interrogator 28. There are also sections to maintain the system personnel and to authorize an expert's system for public use. The listing for the program for the system appears at the end of the specification as Appendix A available within the application file wrapper and is written in FORTRAN 77 for a VAX 780.

To set up the system, the first step, as shown in block 11, is having an expert or panel of experts ("chief") determine all possible revelant input parameters and action options (output recommendations) that the system will use in the teaching and application of a particular expertise. The chief must acknowledge all possible variables, whether or not he/they would consider all variables as necessary to the decision process. The reason is that different experts teaching the process independently might consider different given parameters to be important or different actions to be preferrable. Further, since the system is using probabilistic determinations based on the simultations previously discussed, an expert might not realize that a particular variable is significant to his decision making process. The system will recognize whether or not a variable is significant to the expert's decision making process. The chief then enters these input parameters and action options (output choices) into the system, and also the access codes and names of the experts or personnel who will be teaching the system their particular expertise.

The second part of the set up procedure, as shown in block 12, involves the teaching of the expertise to the system, by the expert. This is accomplished by entering a tree of relational questions, i.e., subsequent questions resulting from the possible outcome of preceding questions. The tree of questions is exactly the way the expert reasons in his own mind when presented with a real case. Each expert who teaches the system developes his own tree of questions. This allows the possibility of having multiple experts on the system for the user to interrogate.

The expert begins generating the tree of questions by entering the root question or entry point into the tree. From the root question, the system will prompt the expert for the next question. This is accomplished interactively between the system and the expert. The system requires the expert to enter the possible responses to each question beginning with the root question. The system then prompts for the subsequent question to each response. When no further questions are needed, i.e., the response to the question is a terminus or output action ("leaf" of the tree) the expert enters the choice from among the output actions that were initially entered by the chief. The list of output actions will automatically appear on the screen in the form of a menu. Each question may lead to a plurality of responses, but each response may only be linked to one parent question. Therefore, a question may lead to several possible responses which can be either subsequent questions or output actions.

Once the expert creates his entire tree, he gets out of the tree creating mode and starts the simulator, or teacher section 20 of the system.

Teacher section 20 is an adaptive simulator. At every question ("node"), the expert is presented with simulated case consistent with the type of cases expected with that part of his decision tree. Simulator 14 starts with the root node and asks the expert to evaluate the case (set of data values) that the system has randomly generated. The simulated cases for the root node are completely random. For each subsequent question, the random number generator is biased (adapted) to reflect the type of data that would be channeled through this branch of the tree. Thus, the system avoids presenting variable values that are inconsistent with the answers previously given. While working down each branch of the tree the simulator will avoid generating data values that conflict with the preceding response to the question. For example, if a question in the system is whether a patient is curable, there would be two branches from this question, Yes and No. Then, when dealing with the branch of the tree for incurable patients (the "NO" branch), the system will avoid asking the expert whether the incurable patient would benefit from a cure, as this is no longer a relevant question, based on the previous answer. For each question in the tree, the simulated cases reflect the answers and significant parameters of all preceding questions along the path from the root questions.

After a number of cases and responses by the expert in block 15 for each question of the decision tree structure independently, the system will build up a statistical base of these simulated cases and will learn which parameters are actually used by the expert in deciding each question. After a sufficient number of cases for each question, the system will be able to determine the significant input parameters for the question to a significance level that the expert desires. For example, if the expert desires a 99% siginificance threshold (confidence level) for each of the parameters that he considers important, he can answer enough simulated cases to determine which parameters become significant to this level. The number of simulations required is determined by how many values there are for each parameter. If there are tens of values for an input parameter, for example, then it would take very many simulated cases to determine the parameter's significance. On the other hand, if there are less than ten values for a parameter, its significance can be determined quicker (usually with a few hundred cases per question).

The expert can monitor the significance of the statistics as he goes along. Every few cases, the expert may check to see what statistics have been accumulated. Once the expert is satisfied with the way that node (question) has been learning by way of block 16, he can move onto the next node and the system will then simulate another series of cases for the expert to evaluate as shown in blocks 17, 19 and 14. When the expert moves on to the next node, the system will generate simulated cases that are consistent with the responses to the preceding questions.

The purpose of using simulated rather than real cases is to avoid problems of correlated variables and to ensure adequate sampling of the extreme parameter values that are possible in a real-life situation. Otherwise, the system would only be responding to the majority of cases and could not generate an accurate probability figure for the extreme cases that might arise when the system is in use. The statistical determinations, significance, and probability, are determined by the chi square and Bayesian probability methods, respectively. The chi square test is used to determine whether a given variable is significant in the expert's choice of responses to the questions. Once the chi square analysis determines the significant input variables, a Bayesian probability table is set up and stored. This table is revised after each teaching session as shown in block 18. When a new case is presented by a user, the likelihood of an answer to a question is determined by the relative values of the products of the Bayesian probabilities of the significant input values for each possible outcome. After the outcome probabilities are calculated for each node of a simulated case, the probability tree is constructed. If the same output action occurs at the end of different branches, then the probability of that outcome action is summed over the individual branch probabilities.

The modifier or editor of the system allows each expert to change his answers for simulated cases previously presented in any node in his question tree. If new development in a given field of expertise show that the expert's choice is no longer valid, the expert can revise previous answers for each node, either (1) case by case, (2) for all cases with a particular recommendation, or (3) for all cases with a particular parameter value. The system will update these records automatically.

To summarize the set up, teaching and modifying sections, an individual or panel (chief) decides all possible input variables and output actions that are possible for a given field of expertise. The chief then enters the name and passwords for one or more experts. Each of these experts would then build his own tree of analysis. These trees consist of questions which mirror the analysis that the expert would go through in person when dealing with a situation that the system is designed to handle, e.g., prostate cancer treatment. The expert sets up his decision tree of questions while being prompted by the system for the number of responses to each question and then the question or output action that serves as a response to the previous question.

Once the entire decision three is set up by the expert, the system begins to learn from the expert through the use of an adaptive simulator. As a succession of simulated cases for a particular question are presented to the expert and answered by the expert by selecting an option from the menu of options for that node, the system begins to learn by determining which input parameters are significant to the expert's analysis. As the expert is questioned further and further down the tree, the simulated cases take into account the responses to the previous questions. When the expert has gone through the simulated cases for each node of the tree, the expert is free to go back and modify the answers to any of the questions (and for any of the cases) based on new developments in the area of expertise, change of opinion, or for any reason that the expert sees fit to change a response. The expert may not change the simulated cases as this could potentially correlate the variables and disrupt the probability analysis.

The fourth part of the system is vertifier 25 which allows each expert to determine the degree to which his system has learned to reproduce his decisions. When activated, the verifier presents the expert with new simulated cases, as shown in block 21. The answers by the expert will be compared, as shown in block 22, with the answers predicted by his tree on the system, and a score will be computed, as shown in block 23. If, for a given case, the end possible answers are determined by the system to have probabilities $P(1), P(2), \ldots, P(N)$, then the score given when the expert choses answer K is $100 * P(K)/max[P(1), \ldots P(N)]$. The verifier presents the expert with the average and standard deviation of the scores attained for all the simulations used in verification. The expert can activate the verifier to check his entire system or each node separately. Once an expert is satisfied that his expert system is functioning reliably, as shown in decision block 24, he can authorize the system for public interrogation.

The fifth part, shown as interrogation 28, involves the interrogation or questioning of the system by the user. To interrogate the system, a user enters a case, as shown in block 26, and choses by menu one of the experts whose system has been made public. Then, as shown in block 27, the system answers questions regarding output actions, the decision process of the experts, significant parameters, trends (rules), and how the preference of the expert would be affected by variations of one of the input parameters. An example of output actions with associated probabilities for the field of prostrate cancer is shown in Appendix B available within the application file wrapper.

The system works equally well in evaluating and comparing the actions taken by multiple users. For example, in the case of hospital care, the input parameters for patients in one hospital would be entered into the system and run through to determine what the expert who designed the system would choose as the most probable treatment. Then, the input parameters for the patients could be evaluated to compare the treatment of patients in one hospital with that of the other. The goal of such an analysis would be to narrow down which aspects of a particular hospital's treatment are more beneficial than that of another hospital.

By maintaining expert systems from experts in different disciplines, the user will have at his disposal the probability of the various experts' decisions for use in his own analysis. An example of this would be an emergency room situation where the decisions of doctors in different disciplines are necessary to evaluate a patient. If an expert system for each discipline was at the disposal of the user, in this case the emergency room physician, an evaluation of the patients' condition could be obtained in seconds or minutes. Thus, the information presented would show the factors, or in this case the condition of the patient, that are significant for each expert's determination of the best treatment.

Figure 2A:
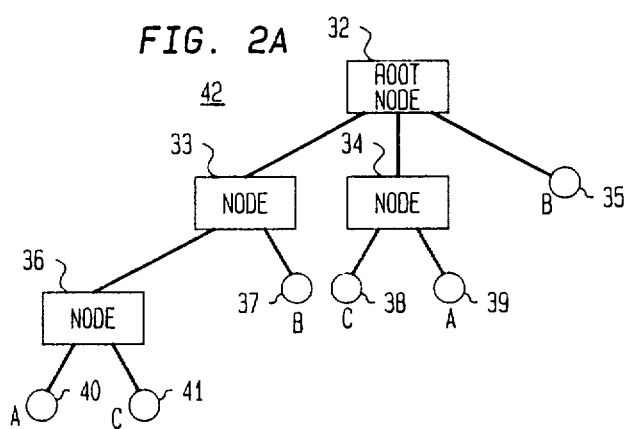
FIG. 2A is an example of a decision tree structure as used in the set up of FIG. 1A.

Referring now to FIG. 2A, there is shown decision tree structure 42. Decision tree structure 42 is illustrative of the linkages of an expert decision tree. Tree 42 begins at root node (or root question) 32. There are three possible responses to root node 32: node 33, node 34 and output action 35. Output action 35 is designated as the B-output action from a possible choice of A, B or C output actions. Node 33, which is an expert decision tree would contain a question, has two possible responses, node 36 and output action 37 (output action B). Block 33's other possible response, node 36, has two output actions as possible responses. These are output action 40 (designated A) and output action 41, (designated C). Node 34 has two output actions as its possible responses. Output action 38 (designated C), and output action 39 (designated A). It is seen that this tree can go on, as necessary, to a particular field of expertise with further questions resulting from the preceding questions until there are finally output actions selected. In decision tree structure 42, there are only three possible output actions, A, B, C. An expert tree may have as many output actions selections as are designated by the chief.

In another embodiment of the invention, a further system may respond to partial information; i.e. an incomplete set of input values which need to be completed before the system can predict an expert's response. It should recognize when missing information is absolutely crucial for a treatment decision and be able to request, in priority of need, exactly those additional pieces of information that will be most essential to the treatment decision.

Neonatal and intensive care monitoring of patients are areas where the potential for partial information decision making is great. In these areas there are several levels of patient monitoring, each more expensive by an order of magnitude than the preceding, with more tests and increased risks of morbidity. To reduce cost and risks, the patient should be kept at the lowest level of care that is warranted. A system which uses partial information would monitor a set of clinical parameters simultaneously, and over an extended period of time at the existing level of care, integrate continually the different variables in terms of the most probable treatment or action decisions of the human expert and alert the human clinician whenever he himself would change treatment, order an additional test, or reduce the level of monitoring.

When there is a possibility of partial information, the system must be trained for both full and partial information situations. Unkown situations are addressed by treating the variables in groups, designated as such by the chief of the particular system application. When the monitored clinical parameters by themselves provide insufficient information to predict the expert's response, at least one of the branches from the decision node will lead to auxiliary nodes that request test to measure the missing groups of variables. The partial information system will thus be a set of overlays, with each overlay containing more information about each decision node than the one below. When complete information is available for a patient, there will be no auxiliary nodes and the system will be able to provide the probability of a given treatment being chosen by the expert. In cases where the system will be able to decide a presented case without full information, it will do so, thus reducing cost and risk.

Figure 2B:
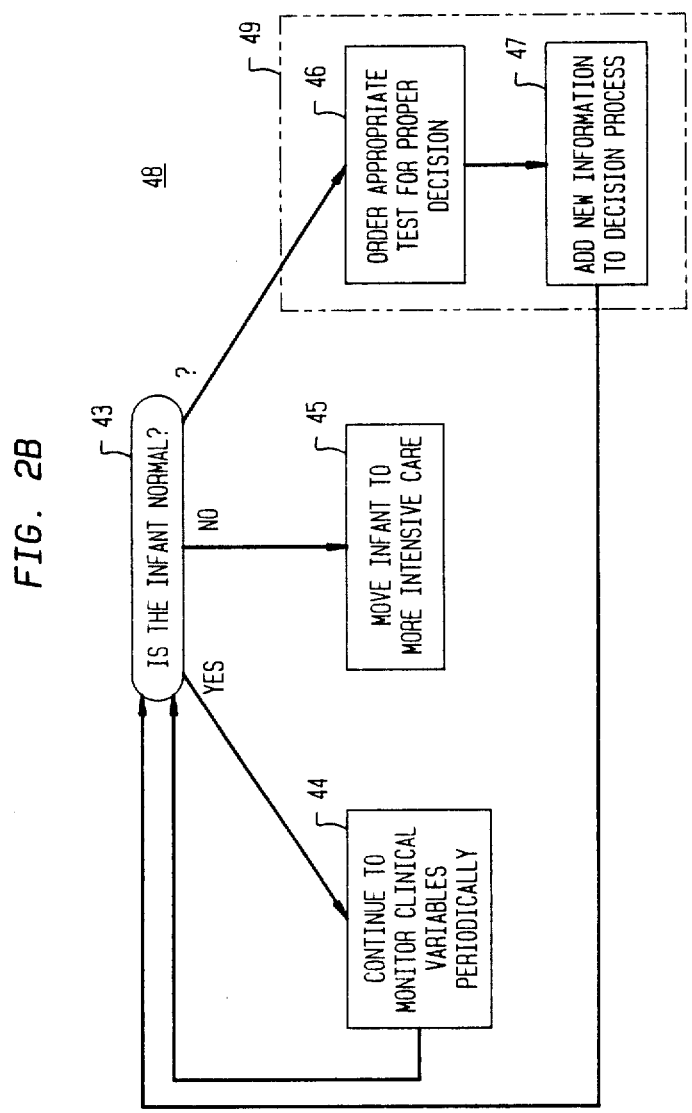
FIG. 2B is a block diagram of a further embodiment of the invention.

There is shown in FIG. 2B, an example flowchart 48 of a neonatal monitoring system. Question block 43, "Is the infant normal!" has three possible responses. The responses are chosen from the group of parameters that are determined to be the minimal necessary for that level monitoring. If there is sufficient information to determine that the infant is normal, question block 43 leads to action 44, "Continue monitoring." If sufficient information is available to determine that the infant is not normal, question block 43 leads to action block 45, "Move infant to more intensive care." However, if there is insufficient information to answer question block 500, question block 43 leads to an overlay which contains action block 46, "Order appropriate test." The system then takes the information that is input from the test requested and, by way of block 47, evaluates the new information and retries answering question block 43. If there is now sufficient information, either action block 44 or 45 will be selected. If additional information is needed question block 43 would lead to an additional overlay which would request additional tests. This will continue until there is sufficient information to reach a decision in either block 44 or block 45.

A still further embodiment is linking multiple experts' systems into an expert system which takes the decisions of each expert system and comes to a decision based on the experts' decisions that were input into it. This would be useful in an emergency room situation where expert decisions in various areas of specialty must be evaulated before a treatment or output action can be taken. This evaluation would be done by the interrogator system (as opposed to a user interrogation) to decide the action priorities and procedural sequences and would have access to all the recommendations of the expert systems fed into it in addition to the data or input values that the individual expert systems are utilizing.

Figure 3:
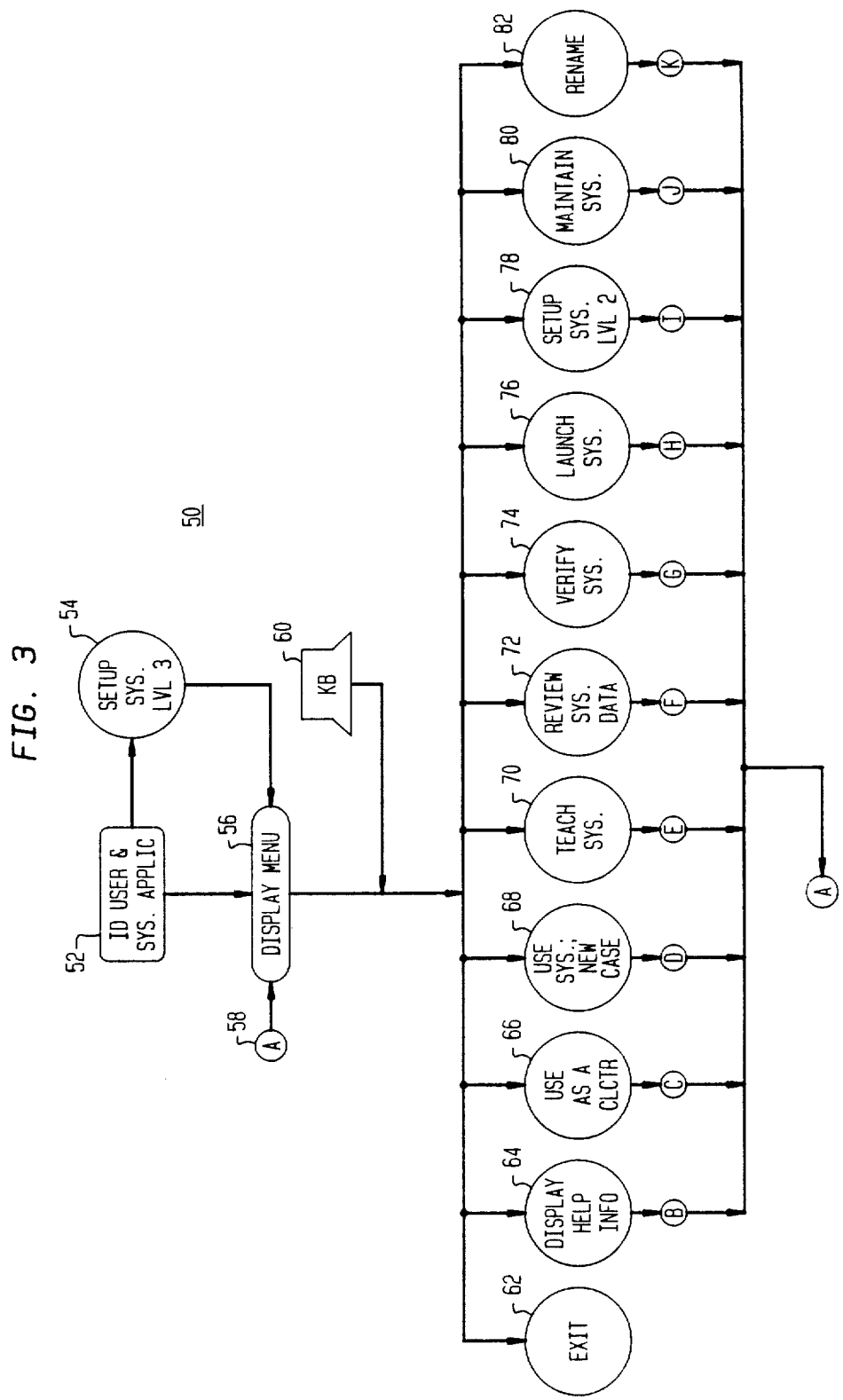
FIG. 3 is an intermediate level flow diagram of FIGS. 1A-B.

Referring now to FIG. 3, there is shown an intermediate level diagram in which the main program is indicated by the reference numeral 50. Execution proceeds at block 52 where the system application program is identified and the user ID is accepted. In response to the display of block 52, the user enters a password. Depending on the password, system I/O may set up a new system application as shown in circle 54. Execution then proceeds to block 56 where the menu is displayed. The menu sets forth the various options which are available to the user depending on the level of the user as determined by the password entered in response to block 52. The levels may be zero, one, two or three. Level zero indicates there is no user identification and program execution stops as shown at exit 62. A level-one password produces the menu options for displaying help information as shown in block 64, permitting use of the system as a calculator as shown in block 66, and interrogating the system to apply expert knowledge to a new case as shown in block 68.

Level two is available to expert teachers. If a level-two password is entered in response to block 52, the options of block 62, 64, 66 and 68 are available. In addition, the user may select the routine for teaching the system as shown in block 70, reviewing system data as shwon in block 72, verifying the system as shown in block 74, authorizing public use of the expert's system as shown in block 76, and setting up the decision tree of the expert teacher as shown in block 78.

Level three is only available to the chief. If a level-three password is entered in response to block 52, the routines available in the menu are blocks 62, 64, 66, 68, 70, 72, 74, 76, and 78 as previously described. In addition, level three provides access to a routine for adding personnel and privilege statuses to the system as well as other system maintenance functions as shown in block 80 and access to the routine for renaming IO quantities as shown in block 82.

With the keyboard 60, the user selects from the various options presented on the menu (defined by the level of the password).

Figure 4:
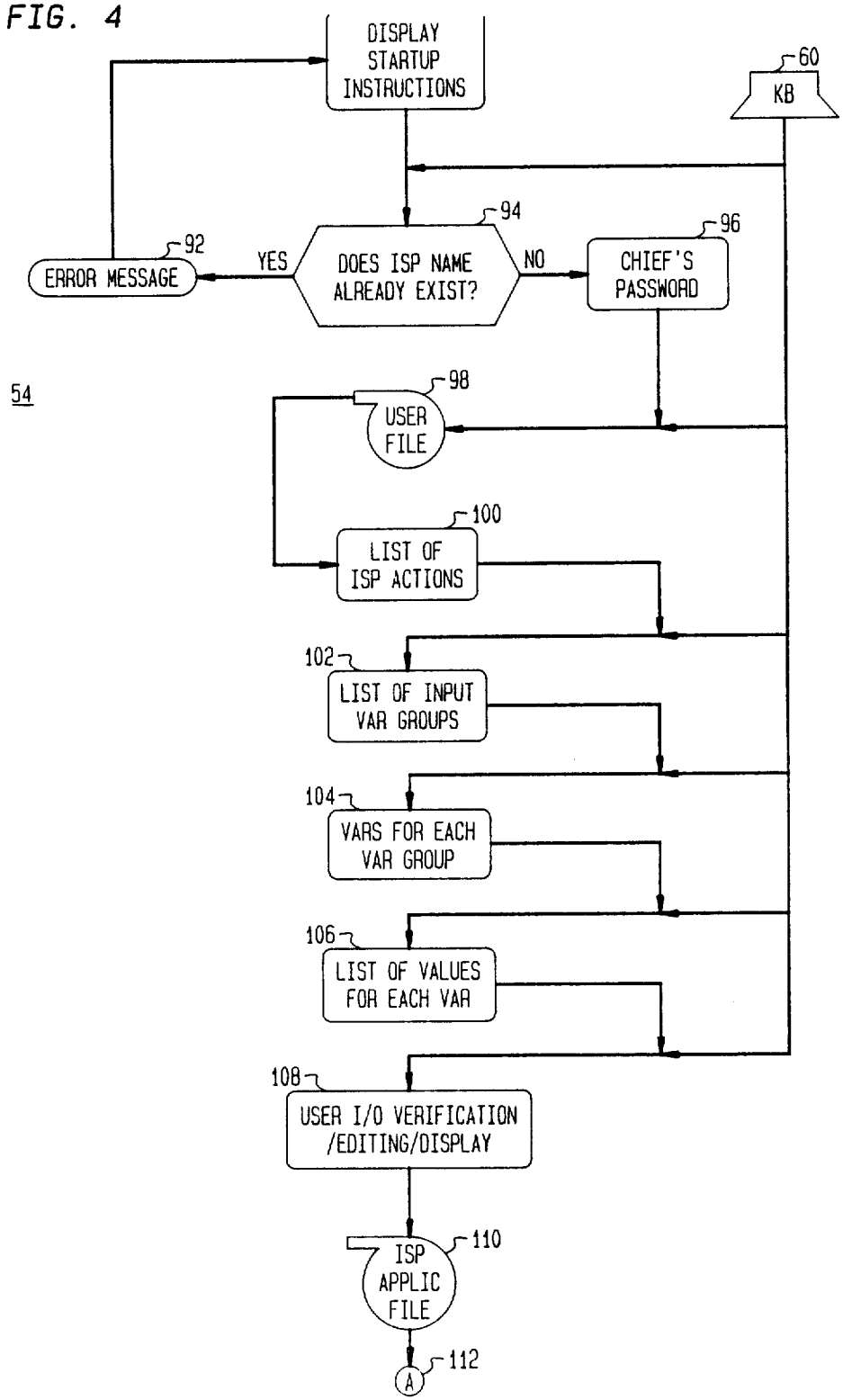
FIGS. 4-11 are lower-level flow diagrams of the aspects shown in the intermediate level flow diagram of FIG. 3.

Referring now to FIG. 4, there is shown a more detailed representation of block 54 which may set up new applications. Execution begin at block 90 where the start up instructions are displayed. These instructions tell the chief how to set up the application. The chief acknowledges these instructions by keyboard, block 60. In decision block 94, the system determines whether or not the name of the new application being set up by the chief already exists. If the name already exists, an error message is displayed as shown in block 92 prompting the chief to provide a new name for the new application. In addition to the name of the application, as the chief enters new names for variable groups, variables themselves, variable values and actions, each will be checked, as shown in decision 94, and an error message generated as shown in block 92, as previously described, prompting the chief to provide a new name.

If decision block 94, indicates that the new name is not being used, the application name is accepted, and the chief is asked to create a password (block 96). A new user file with the name entered by way of the keyboard (block 6) is created along with the password of the chief and the new application name as shown at input 98.

A block 100, the system requests a list of all output actions that the new system application may ultimately recommend. A list of all of the variable groups is requested in block 102. These variable groups may be groups of clinical variables, blood variables, etc. In block 104, a list of the variables is requested and in block 106 a list of all of the possible variable values for each variable is requested. As previously described, the information requested by blocks 100, 102, 104, 106 is entered by way of the keyboard as shown in block 60 and are checked to determine that names entered do not already exist as shown in decision 94.

In block 108, a menu of options to edit the input list of names is provided to permit user verification, editing and display of sytem I/O options. The application file is created once the procedures of block 108 are completed, as shown in block 110, and execution proceeds by way of off-page connector 112 to routine 50.

Figure 5:
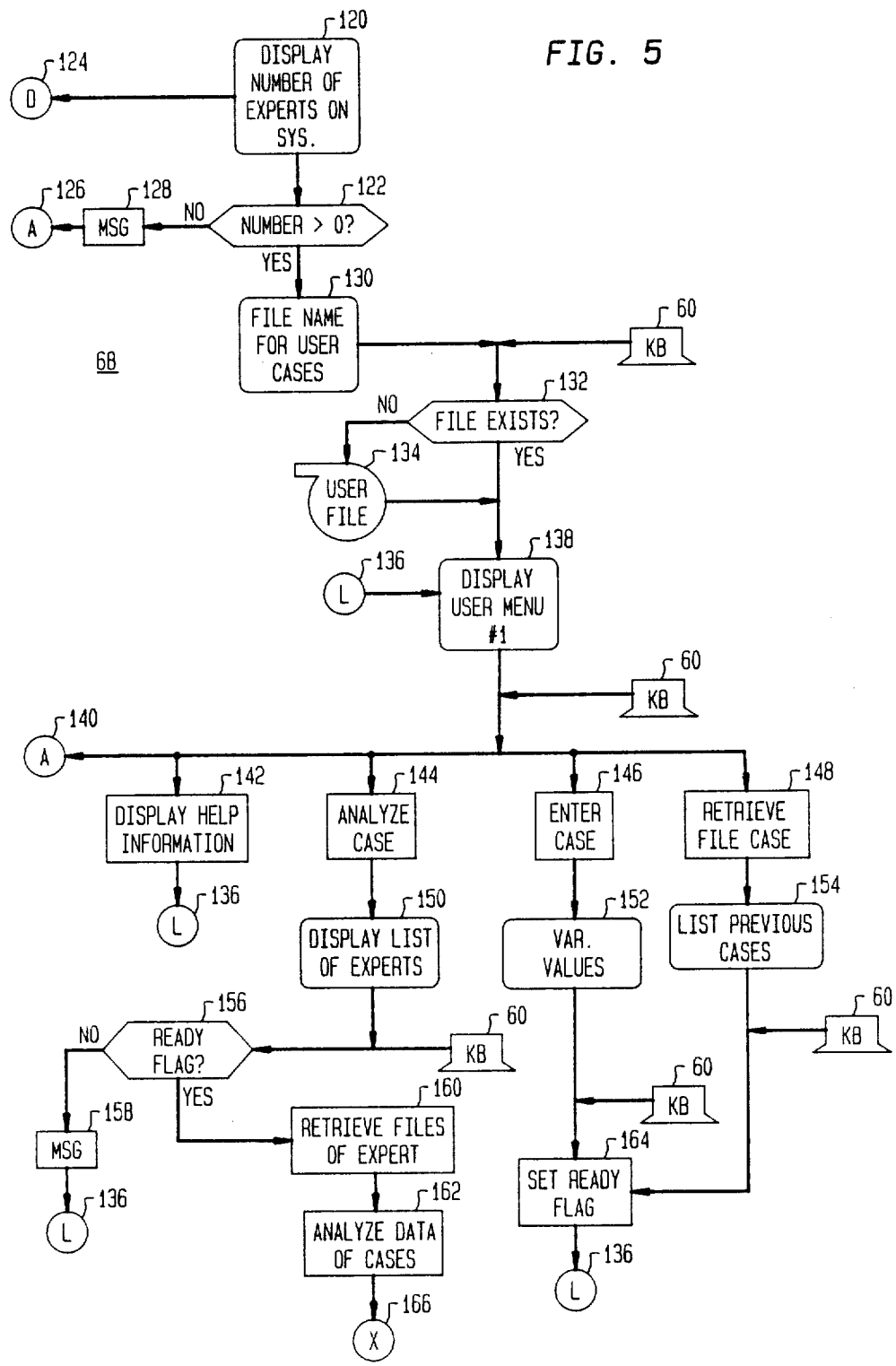

Referring now to FIG. 5, there is a shown a more detailed representation of block 68. Execution begins at block 120 where the system displays the number of experts on the system. This number is the number of teachers who have authorized their database for public use. If no experts have authorized their system for public use as determined as decision 122 a messae is provided to the user as shown in block 128 and execution proceeds by way of off-page connector 126. At block 130, the system requests the user to supply a file name for the user cases to be entered. This permits the user to store several cases and allow repeat use of a case for several different experts. The user enters the desired name by using the keyboard as shown in block 60 and at decision 132, the system determines whether that file name already exists. If that file name does not already exist as determined by decision 132, the user file is created as shown in input 134.

At block 138, user menu #1 is displayed for option selection by the user by means of keyboard 60.

The options available to the user at a return to the main program by off-page connector 140, display of help information, as shown in block 142, including an option to select a return to display menu #1, block 138, by way of connector 136, and analysis of the case entered as shown in block 144. Additionally, the user may enter a case as shown in block 146 or retrieve a file case as shown on block 148.

If the user selects a case analysis, block 144, a list of experts is displayed as shown in block 150. The user selects the expert desired by use of the keyboard as shown at block 60. A determination is made in decision 156 whether the ready flag is set. The ready flag is set when a case is entered and analysis of a case cannot begin unless this flag is set. If the ready flag is not set as determined in decision 156, a message is provided to the user and execution proceeds back to the user menu display as shown in block 138 by way of connector 136.

When the files of the requested expert are retrieved as shown in block 160, analysis of the case begins as shown in block 162 and execution proceeds by way of connector 166.

If the user elects to enter a new case in response to the menu of block 138, a display menu of possible values is shown for each variable of the new case in sequence, as shown in block 152. The user selects values from each variable by use of keyboard block 60 from the list of possible variable values, following which the ready flag is set as shown in block 164. Execution then proceeds back to the display of the user menu #1 as shown in block 138 by way of connector 136 to permit the user to have the case analyzed as shown in block 144, if desired.

The menu of block 138 allows the user to retrieve a file case as shown in block 148. In response to a selection of this option, a list of the previous cases is displayed, as shown in block 154, permitting the user to select by keyboard, block 60, one of the file cases displayed. When a case is selected, the ready flag is set as shown on block 164 and execution again proceeds back to block 138 where the menu is again displayed.

Figure 6:
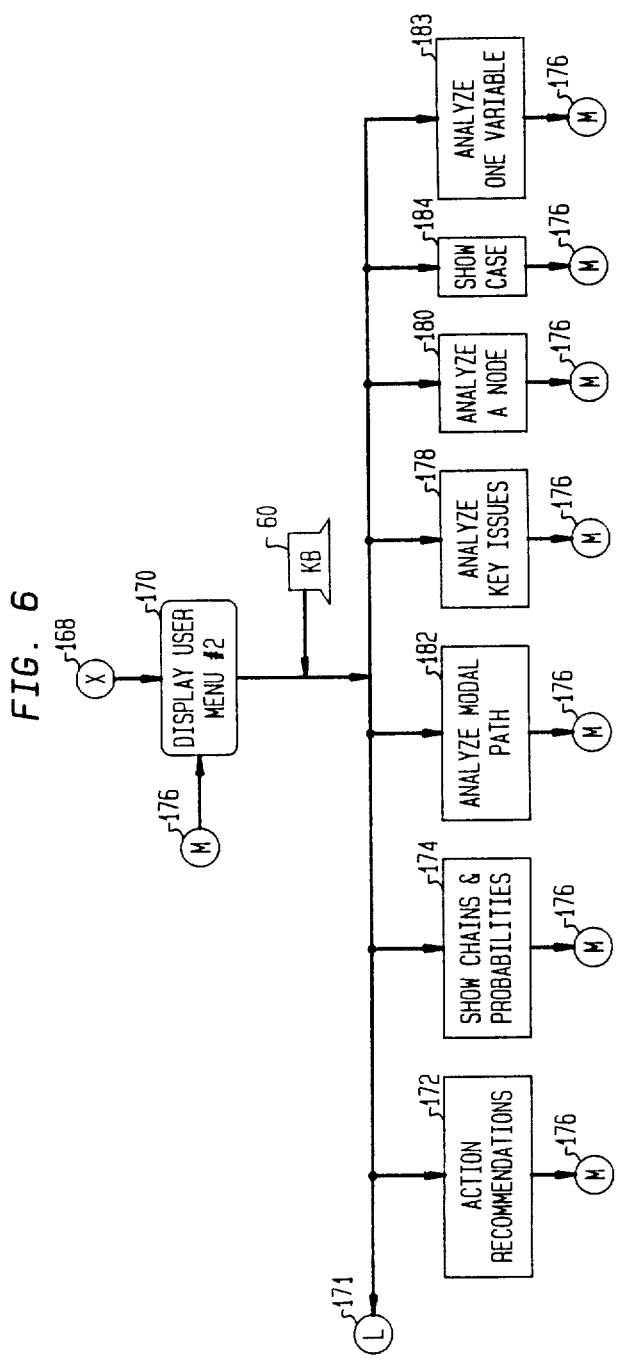

Referring now to FIG. 6 there is shown a continuation of routine 68. Execution proceeds from connector 166 of FIG. 5 to connector 168 to proceed with analysis of the case. User menu #2 is displayed as shown in block 170. By keyboard block 60 the user may return to the previous display of the user menu of block 138. Alternatively, the user may request the recommendations that the expert would make along with the probabilities for each recommendation as shown in block 172. These action probabilities will be arranged in the order of descending probabilities. The user may also request all chains of reasoning and the probabilities of each chain as shown in block 174. This selection will provide each path through the decision tree along with the decision probability of each node on the path, arranged so that the modal path is displayed first.

The modal path may be further analyzed by the user by selecting block 182. This choice causes the system to display the probability of the modal path. For each node along the modal path in the decision tree, the significant variables are displayed and their significance levels are provided. These include the most significant variables that the expert uses in deciding the question, the probability of each branch from the node, and the variable values that strongly indicate or prohobit the recommendation of the modal path.

As shown in block 178 in response to the menu displayed in block 170, the key issues of the case may be analyzed. This choice sorts the probabilities for arriving at the leaves of the decision tree and flags all the nodes on the decision path to the most important leaves of the decision tree. The probabilities of arriving at the flagged nodes are sorted and the key issues (nodes with exceptionally large or small Bayesian probability) are displayed for the flagged nodes. A single node in the decision tree may be analyzed by selecting block 180 from the menu displayed in accordance with block 170. If this option is selected, the user is asked to select (by menu) a node in the decision tree. For the selected node the probability of reaching the node is displayed along with the significant variables and the recommendations for the mode output branches on the assumption that this node has been reached. In addition, the Bayesian probabilities for each significant variable of the presented case are provided for each branch from the node. The key issues in deciding or prohibiting a branch from this node are also displayed.

As shown in block 183, the user may observe how changing the value of one variable affects the action recommendation of the expert. The user selects a variable from a menu presentation and the system displays the action recommendations of the expert for each possible value of the chosen variable. The caes being studied by the user may be displayed by selecting the option of block 184.

If the option of block 172, 174, 178, 180, 182, 183 or 184 is selected after the actions described above, execution returns to block 170 by way of connector 176, causing the user menu to be displayed again.

With respect to block 180, the analysis of a node in the decision tree is a four-step process. In the first step, the probabilities for the variable values of a given case are retrieved and accumulated to find the total probability of each link (branch). This is performed for each significant variable of each variable group used by the node. For each node in the expert's decision tree with at least two output link, the resultant value is determined for each link and the probabilities of the output links of a node are normalized so that the sum is 100%. This provides the output probabilities for each node in the expert's decision tree.

In the second step all link probabilities leading from the present node to the root of the tree for each node in the expert's decision tree are multiplied. This provides the probabilities with which the human expert would arrive at each node.

In the third step for each leaf node of the decision tree, step 2 is repeated. This provides the probabilities with which the human expert would arrive at each leaf node in the decision tree.

The probabilities of the leaf nodes with the same action decision are added in step 4. This provides the probabilities of each action of the human expert for this case.

From the teaching system, the computer has found and stored all values of $P_{ijmnl}$, where i is the variable group index, j is the variable index, m is the variable value index, n is the node index, and l is the index link from the node. Thus $P_{ijmnl}$ may be defined as the probability of action link l from node n for value m of variable j of variable group i. The set of values of $P_{ijmnl}$ may be written as follows:

$$\{P_{ijmnl}: i\epsilon[1,N_g]; j\epsilon[1,N_p(i)]; m\epsilon[1,N_v(i,j)]; n\epsilon[1,N_d]; l\epsilon[1,N_L(n)]\} \quad (1)$$

where $N_g$ i equal to the number of variable groups, $N_p(i)$ is the number of parameters or variables in variable group i, $N_v(i,j)$ is the number of possible values of variable j of group i, $N_d$ is the number of nodes of the decision tree, and $N_L(n)$ is the number of links emanating from node n. The notation $i\epsilon[1,N_g]$ denotes one $<i<N_g$, etc.

If we define X by the product $$X(n,l) = \prod_{i=1}^{N_g} \prod_{j=1}^{N_p(i)} P_{ijmnl}$$

restricted to those variables (i,j) which are statistically significant and used in node n, the probability that link l from node n is chosen by the human expert for a presented case is $P_L(n,l)$ $$P_L(n,l) = \frac{X(n,l)}{\sum_{l\epsilon n} X(n,l)}.$$

Actually equation (2) is determined by summing over logarithms and subtracting the smallest log of X(n,l) before taking the antilog.

Thus in step (2) of block 180

$$P_N(n) = \prod_{n'=n}^{n'=root} P_L(n',1)$$

wherein the product is taken over all the nodes and branches leading from the root node to node n.

In step (3) of block 180

$$\{P_C(n)\} = \{P_N(n): n \text{ is a leaf node}\} \subset \{P_N(n)\}$$

$P_C(n)$ is the probability of arriving at a leaf node.

In step (4) of block 180

$$P_A = \Sigma P_C(n)$$

where $P_A$ is the probability the human expert will choose action A for the case. It is the sum of the probabilities of all leaf nodes in the decision tree which have output action A.

Returning now to user menu #2, displayed for block 170, selection of the option of block 172 provides $P_A$ for each action A. Selection of the option of block 174 provides $P_C(n)$ for all n=leaf node and $P_L(n,l)$ for all chains.

Selection of the option of block 182 provides $P_C(n)$ for all n in the chain with the largest $P_C$ and $P_L(n,l)$ for each n of that chain (from leaf node to the root node) and shows the significant variables.

$P_C(n)$ for the most probable chains are retrieved when the option of block 178 is chosen. Then the nodes n of the most probable chains are flagged and sorted. For each flagged node, in order of largest $P_N(n)$, a search is performed for $P_L(n,l)>$threshold. Then the output link (n,l) is listed in words showing the node and key variables of the node which indicate output l. A sort is performed according to $P_L(n,l)$.

When the option of block 180 is selected $P_N(n)$ is shown, as well as $P_L(n,l)$, for all l of node n. Additionally the significant variables are given and the action probabilities are provided on the assumption that node n is the root node. The Bayesian probabilities are displayed for each significant variable (i,j) for each output link l of node n assuming m is given by the case presented. Those variable values that prohibit an output link are shown along with the variable values that strongly indicate the link.

When block 183 is selected, the user picks a variable (i,j) as previously described. For each possible variable value m of variable (i,j), the action probability $P_a$ is shown for each action A. This requires recalculation of the $P_A$ values as the variable value changes.

Figure 7:
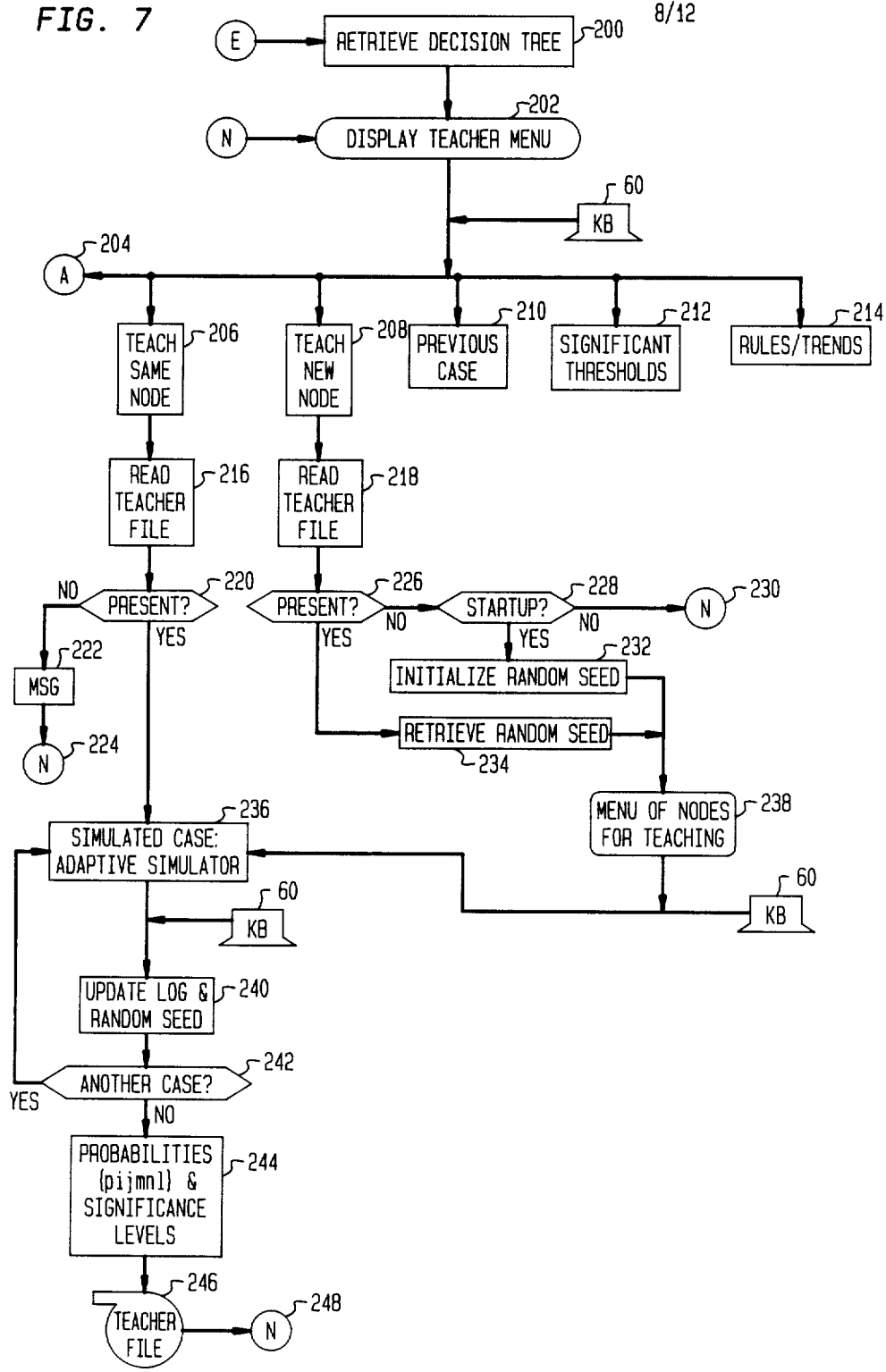

Referring now to FIG. 7, there is shown a more detailed representation of block 70 which is selected when a user wishes to teach the system. Execution begins at block 200 where the decision tree of the expert teaching the system is retrieved. In block 202 the teacher menu is displayed and an option on the menu is selected using keyboard 60, as previously described. The options which the teacher may select are set forth in block 206, 208, 210, 212 and 214, as well as a return to the menu of block 56 in FIG. 3 by way of off-page connector 204. These options briefly are: to continue teaching the same node (block 206) to teach another node (block 208), to edit a previous case (block 210), to set variable significance thresholds (block 212), and to check the data for rules and/or trends, thereby checking whether the system has learned any rules or key issues, as shown in block 214.

If the option of block 206 is chosen, execution proceeds to block 216 where the teacher's file is recalled. In decision 220, determination is made whether the file requested is present. If the file requested is not present, as determined in decision 220, a message is provided to the user (block 222) and execution proceeds by way of connector 224 to block 202 where the menu is again displayed.

If the file requested is present, the last random seed and case number is read and execution proceeds to block 236 where another simulated case is created. The adaptive simulator of block 236 adjusts the cases to the node being taught. Thus an improbable case for a given node may be avoided.

In block 240 a random seed is provided and the log is updated. If another case is to be provided as determined in decision 242, execution returns to block 236.

When the teaching session is over, and/or no further cases are needed, execution proceeds to block 244 where the probabilities $p_{ijmnl}$ and chi-square significance levels for each variable of the node are determined. For each variable, a chi-square table is provided in which the system tabulates the number of cases for each parameter value for each output link of the node. The system then again checks for rules and trends. The Bayesian probabilities are calculated for the node n being taught under the starting assumption that all output links are equally possible a priori.

The probability of value m of variable (i,j) if it is known that the output link of node n is 1 is found from the simulated data as follows:

$$p(m|1) = \frac{N_{m1}}{\Sigma N_{r1}} \; ; (i,j,n \text{ fixed})$$

Where $N_{r1}$ is the number of case with variable value r and output link 1, and the summation is over index r from one to the maximum number of value of variable (i,j). The probability of output link 1 of node n if the variables (i,j) has a value m is from Bayes Theorem:

$$p(1|m) = \frac{p(m|1)p(1)}{\Sigma_s p(m|s)p(s)} \; ; (i,j,n \text{ fixed})$$

where the summation is over the index s for the output links of the node and where p(l) is the a priori probability that the expert will choose action 1, that is, a probability assumed to be known independently from the simulated data. However even though p(l) is assumed to be known a priori, it is actually unknown for any of our applications. Thus the value for p(l) is chosen to be the same for all 1. Thus:

$$p(1|m) = \frac{p(m|1)}{\Sigma p(m|s)} \; ; \text{(the sum is over } s\text{)}$$

so that the action probabilities are estimated solely by simulated data as taught by the teacher. The advantage of this is good pattern recognition for (no bias against) actions that are used infrequently.

The teacher file is then stored as shown in block 246 and execution proceeds by way of connector 248 to block 202 where the teacher menu is again displayed.

If the teacher wishes to teach a node as shown in block 208, the teacher file is recalled as shown in block 218. A determination is made in decision 226 whether the file requested is present. If the file is not present, a determination is made whether this is a start-up at decision 228 and if not, execution proceeds by way of connector 230 to display the menu again in block 202. If the file was present as determined in decision 226, the random seed is retrieved, and if it was a start-up as determined in decision 228, a random seed is intialized in block 232. In either case, in block 238 display is provided of the allowed accessible nodes for teaching. The user may select one of these nodes using the keyboard as shown in block 60. When a node has been selected execution proceeds to block 236 where a simulated case is created as previously described.

If the teacher wishes to edit a previous case and selects block 210, the teacher may change the decision for any previously taught case. This allows updating of the system if new information becomes available. After revising one or more cases, files are updated.

Variable significance thresholds may be set by selecting block 212 of the display menu as previously described. In this routine, the teacher can set a single significance threshold for all the variables at once or a separate threshold for any individual variable. This allows the teacher to set low thresholds initially and raise thresholds as the ISP learns. Also the teacher can monitor the learning process and raise or lower the thresholds for elimination or inclusion of specific variables.

During the teaching process, data can be checked for rules and trends using block 214, also as previously described. This is useful since during the teaching process certain variable values may become so significant that they influence the chi-square calculation and become rules or trends. Thus, for example, for prostate cancer when a patient is not potent a particular expert never uses an implant treatment.

Figure 8:
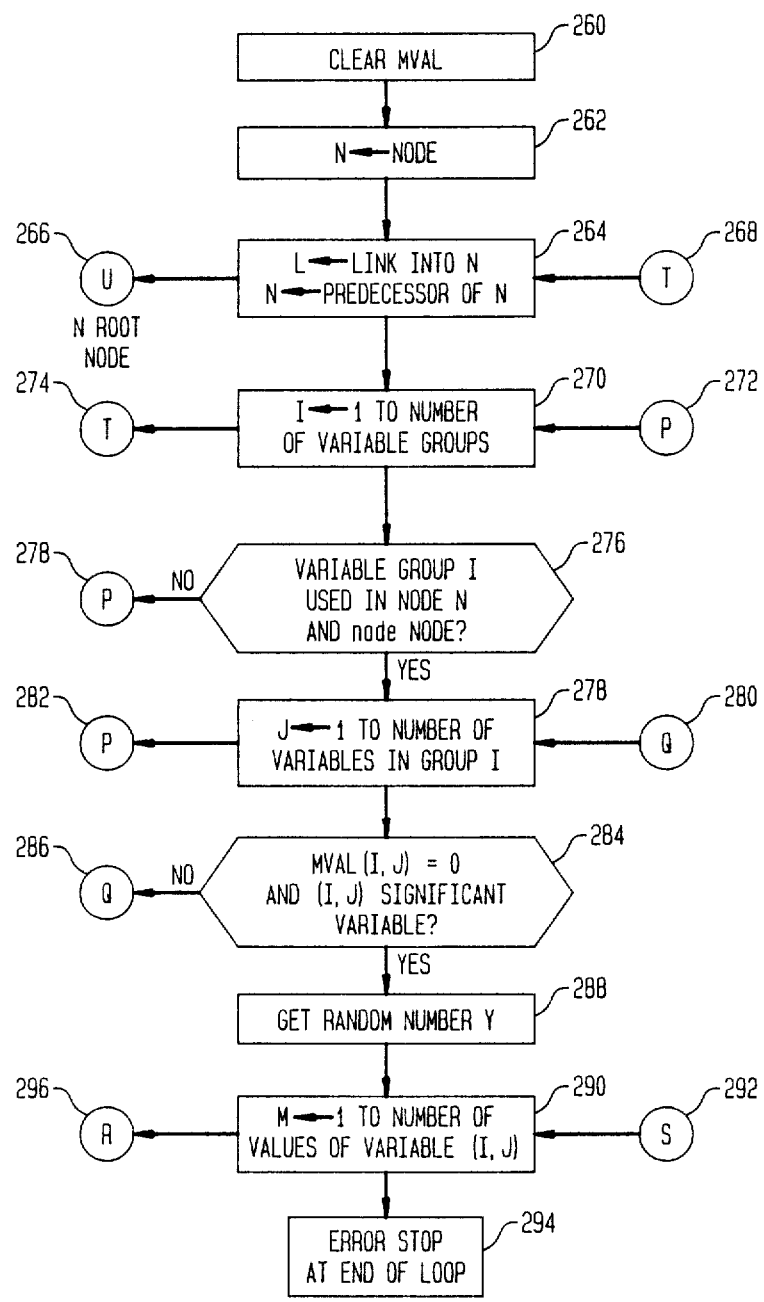

Referring now to FIG. 8, a more detailed representation of the adaptive simulator of block 236 is shown. Execution begins in block 260 where the array MVAL is cleared and N receives the value of the node being taught. In block 264, L receives the link into N and N receives the predecessor of N. Block 270 begins a loop running from one to the number of variable groups and within the loop having I for an index. A determination is made at decision 276 whether the variable group I is used in node N and node NODE. If the answer is negative, execution proceeds by way of connector 278 through connector 272 iterating the I loop. If the answer to the determination of decision of 276 is Yes, a J loop is begun in which the J loop runs from one to a number of variables in group I. The first decision made within the J loop is decision 284 in which a determination is made whether MVAL(I,J) is zero and whether (I,J) is a significant variable. If the answer to this determination is No, execution proceeds by way of connectors 286, 280 to increment J and thereby proceed through the J loop. If the answer to the determination of decision 284 is Yes, the random number is read in block 288 and in block 290 an M loop is begun in which M runs from one to the number of values of variable (I,J). When M has been fully iterated, an error condition exists, as shown in block 294. When the J loop is fully iterated, execution proceeds by way of connectors 282, 272 to increment the I loop. When the I loop is fully iterated, execution proceeds by way of connectors 274, 268 to block 264 to assign values to L and N as previously described. When N is a root node, execution proceeds by way of off page connector 266 to on page connector 300 of FIG. 9. Returning however to the M loop of FIG. 8, execution proceeds by way of connector 296 and on page connector 301 to block 310 where a probability is determined for value M of variable (I,J) of link L of node N. The cumulative probability is determined in block 312 and a determination is made in decision 314 whether the cumulative probability is greater than the random number Y. If the answer to the determination of decision 314 is Yes then MVAL(I,J) is assigned the value M in block 316 and execution leaves the M loop by way of connectors 318, 280 to increment the J index and continue in the J loop.

If the determination of decision 314 is negative, execution proceeds by way of connector 315 and connector 292 to increment the M index of the M loop.

Figure 9:
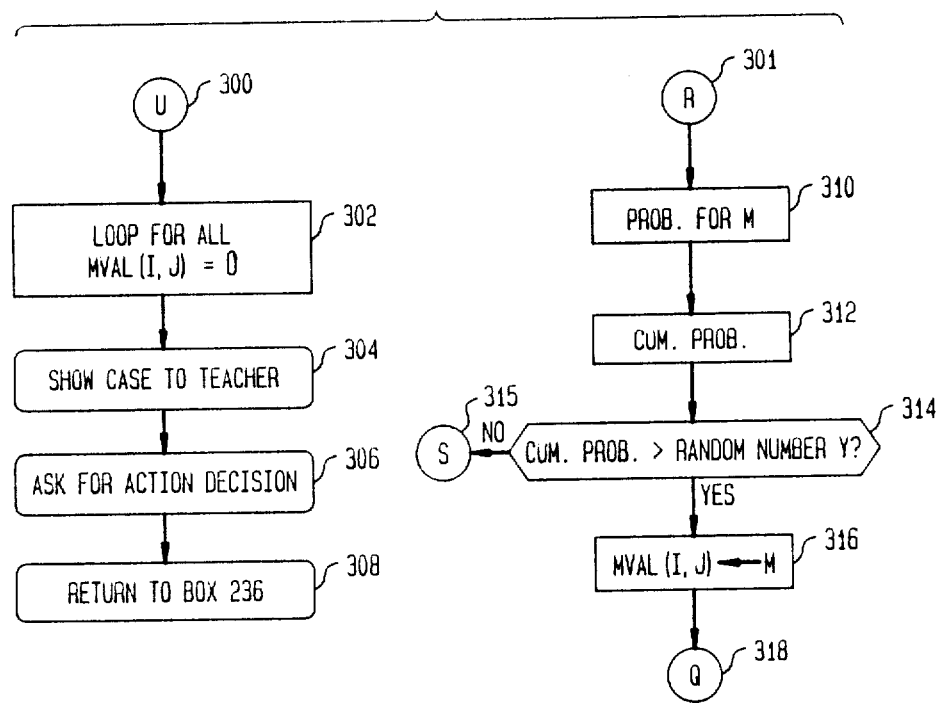

Assuming all loops are properly iterated and the root node is reached, execution proceeds from off-page connector 266 of FIG. 8 to on-page connector 300 of FIG. 9, as previously described. In block 302 the I and J loops, as previously described, are looped again for all values of MVAL(I,J) which are still zero, i.e. for variables which are not statistically significant. An equal probability is then chosen for each value and the random number is used to assign a value to each variable. The case is then shown to the teacher as shown in block 304 and an action decision is requested in which the menu of output links from each node is shown. Execution then proceeds to block 236 where a simulated case is created, as previously described.

Figure 1B:
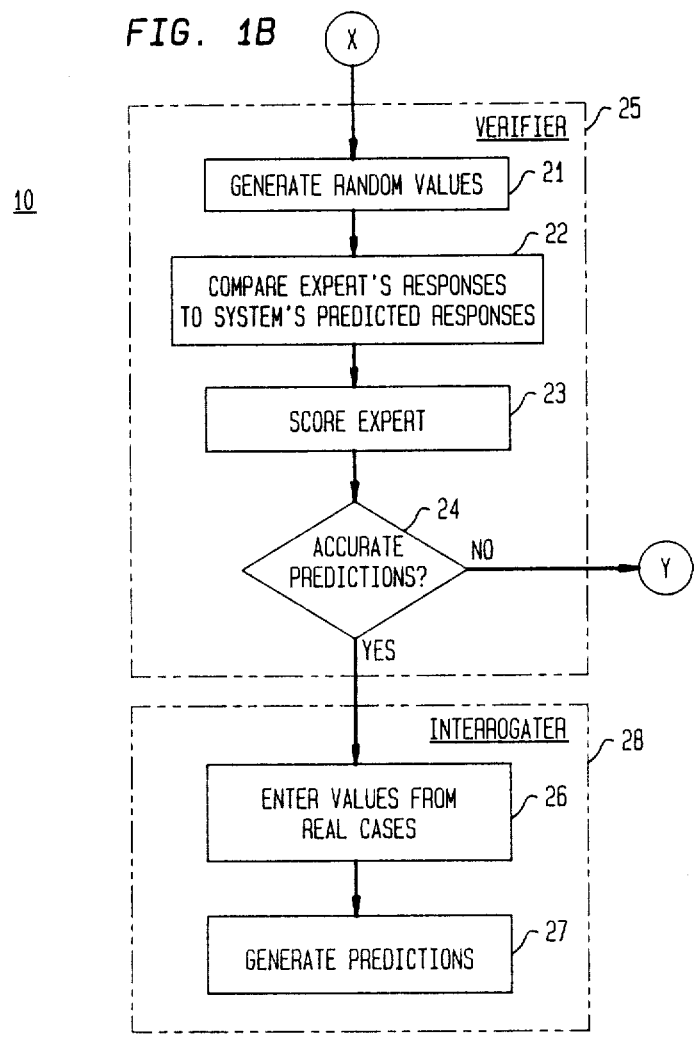
Figure 10:
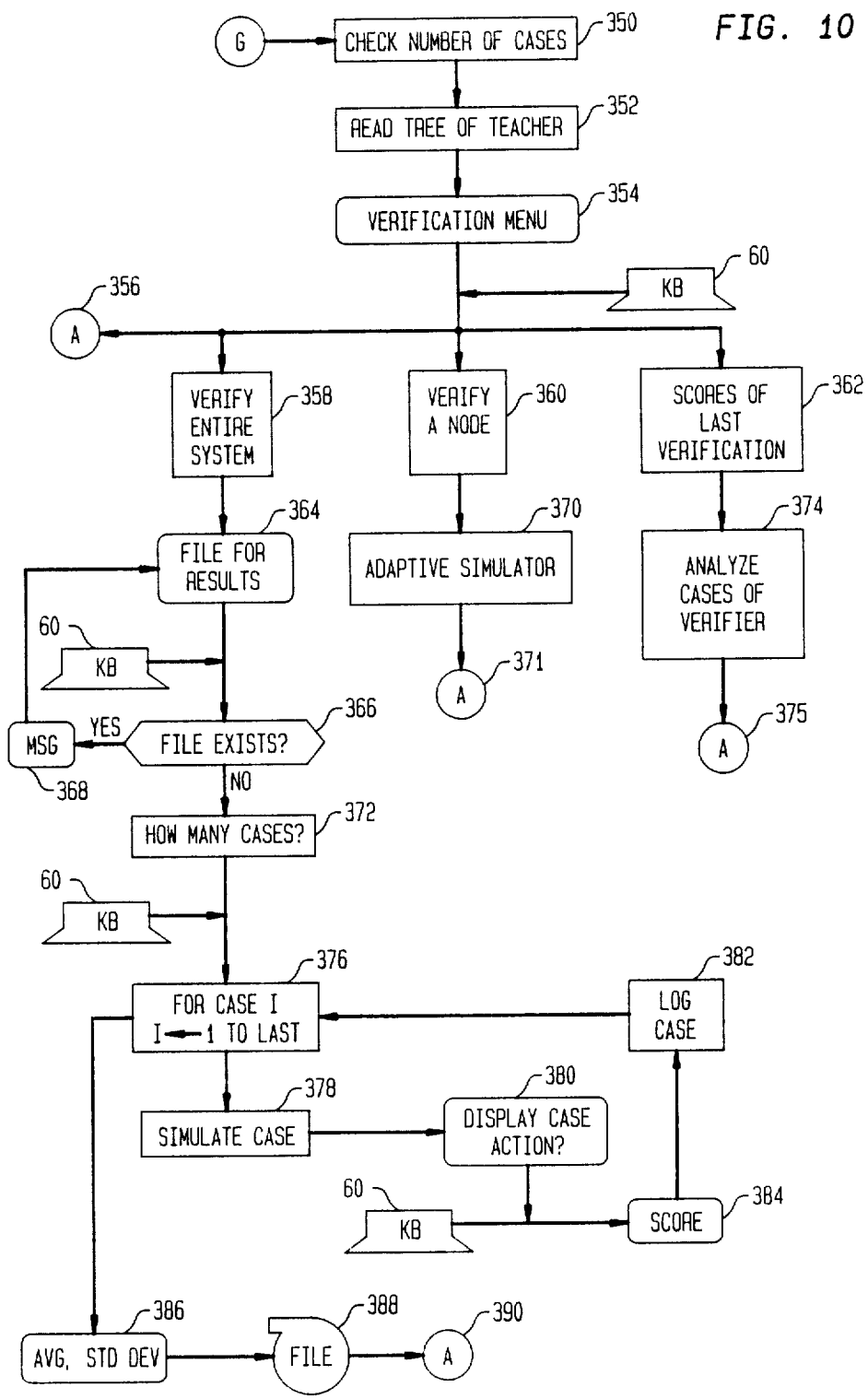

Referring now to FIG. 10, a more detailed representation of the verification of the system of block 74 is shown. Execution begins at block 350 where a determination is made whether all the nodes in the teacher's decision have been taught with at least 25 cases. If an adequate amount of teaching has been performed, as determined in determination 350, the tree of the teacher is read in (block 352) and a verification option menu is provided as shown in block 354. One of the options of the verification menu is selected by means of the keyboard as shown in block 60. These options include a return to the original menu of FIG. 1 by way of off-page connector 356, a verification of the entire system in block 358, a verification of a node of the tree in block 360 and a display of the scores of the last verification as shown in block 362.

If the entire system is to be verified, the user selects the option of block 358 and the system requests a file name to store the results of the verification as shown on block 364. The user presents a file name using keyboard 60 and a determination is made at decision 366 whether the file name already exists. If the file name does already exist, as determined in decision 366, a message is provided to the user in block 368 and another request for a file name is presented to the user in block 364. When a suitable file name is selected, execution proceeds to determination 372 where the user is requested to enter the number of cases he wishes to generate to verify that the ISP can reproduce his judgment. The user enters the number of cases using keyboard 60 and an indexed loop is opened at block 376, in which a simulated case is provided in which all variable values are equally probable. The case is displayed and the user is asked to enter an action by way of keyboard 60. When the user enters an action, a score is determined in block 384 according to the following:

$$\text{score} = \frac{p_i}{\max \{p_j\}}$$

where $p_i$ is the system probability of the system choosing the action I selected by the (human) verifier. The case is then logged as shown in block 382 and the I index of the loop is incremented in block 376. When the indexed loop is complete, execution proceeds to block 386 where an average and standard deviation are determinated for the scores and the file is then stored in output 388. Execution then proceeds by way of connector 390 to connector 58 of FIG. 3.

If only a node is to be verified rather than the whole system, the option of block 360 is selected from the verification menu provided in block 354. Execution proceeds from block 360 to block 370 where a verifying routine similar to that described for the verification of the entire system is performed but using the adaptive simulator to simulate each case of the node chosen by the menu. Upon completion of this, execution proceeds by way of the connector 371 to connector 58 of FIG. 3.

The option of block 362 permits the scores of the last verification to be displayed as shown on block 362. This allows the teacher to analyze the cases presented by the verifier as shown on block 374. When complete, execution may proceed by way of connector 375 and return to connector 58 of FIG. 3.

Figure 11:
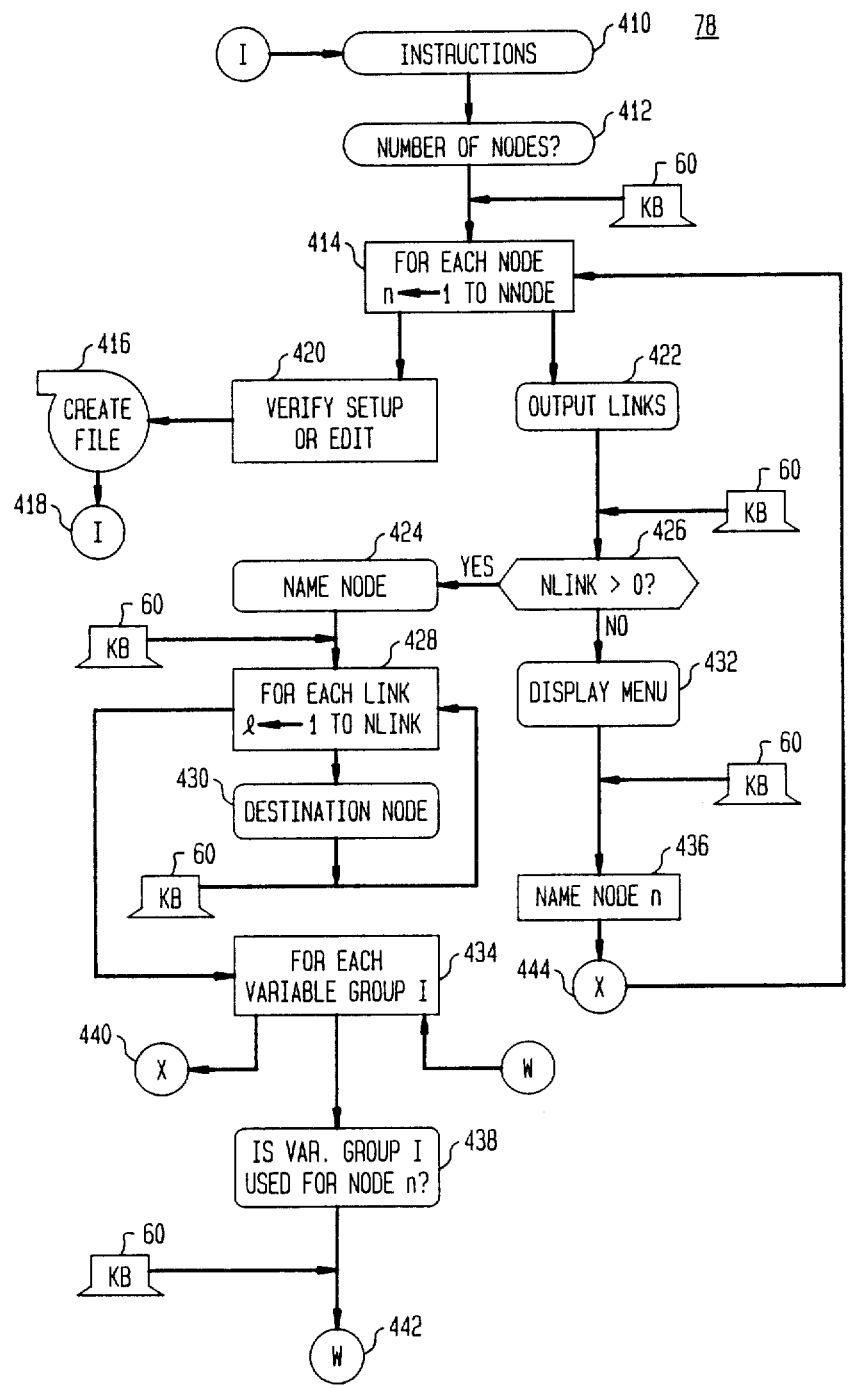

Referring now to FIG. 11, a more detailed representation of the set-up of the system of block 78 is shown in which a set-up decision tree is constructed. Execution begins at block 410 in which instructions are displayed. At decision 412, a determination is made how many nodes are to be set up. When the expert constructing the decision tree enters the number of nodes, an indexed loop is begun at block 414 to set up each node of the tree. The first item in the loop is a question in determination 422 wherein the user is asked how many output links are to be set up for the node n. The user enters the number of output links by way of a keyboard and this value is assigned to the variable NLINK. In decision 426, a determination is made whether NLINK is greater than zero. If NLINK is not greater than zero, a display of the menu of system action options is provided in block 432 and the selection is made by the user by means of keyboard 60. In block 436, the node n is given the appropriate action name by the system and execution proceeds by way of connector 444 to the beginning of the indexed loop. If NLINK is greater than zero, the person setting up the decision tree is asked to name the node in block 424. The name of the node is entered by wy of keyboard 60 and another indexed loop is opened at block 428 in which L proceeds from one to NLINK for each link. The new loop requests the destination node of the links as shown in block 430. The person setting up the decision tree enters the destination node of each link by means of keyboard 60. Execution then proceeds to block 434 where another indexed loop is begun, requesting an answer to the question whether variable group I is used for node n. Thereby this question is answered for each variable group. When this question is answered for each variable group, execution leaves the loop of block 434 and proceeds by way of connector 440 to the end loop of block 414.

When the end loop of block 414 is complete, execution proceeds to block 420 in which the teacher may verify the set-up, or edit as needed, using the previously described menu. When this is done, the teacher's tree file is stored as shown in output 416 and execution proceeds by way of connector 418 to FIG. 3.

We claim:

1. A method for generating an expert system comprising the steps of:
   (a) establishing a set of input parameters having input values which define a case situation and establishing a set of output actions in which the relationship between each input parameter and each output action defines a combinatory situation;
   (b) establishing a decision making structure formed of linked nodes with specified nodes defining questions;
   (c) generating random values to serve as input values defining a first case situation for a first node;
   (d) responding by the expert to the questions posed at the first node;

(e) generating a new set of random values to serve as new input values defining a new case situation for the first node;

(f) repeating steps (d) and (e) until a sufficient number of responses having a predetermined statistical significance is achieved for the first node;

(g) generating in turn for each node subsequent to the first node new random values defining a further new case situation biased by a function of a response from a preceding node;

(h) responding by the expert to the questions posed at each subsequent node;

(i) generating a new set of random values as in step (g);

(j) repeating steps (h) and (i) until a sufficient of responses having a predetermined statistical significance is achieved for each of the subsequent nodes.

2. The method of claim 1 in which step (g) includes generating random values which are consistent with the preceding responses.

3. The method of claim 1 in which step (g) includes generating non-biased random values for a first node in the linked node structure.

4. The method of claim 1 in which step (c) includes grouping the random values into a set of values defined as a simulated situation to be responded to in step (d).

5. The method of claim 1 in which step (d) includes responding to the nodes based upon the random values of the input parameters.

6. The method of claim 1 in which there is provided the further step of generating one set of random values, responding to the set of random values at each node, independently predicting the response to the random values of the input parameters based on step (e), and comparing the response to the set of random values to the predicted response.

7. The method of claim 1 in which step (b) includes establishing a plurality of decision making strctures each for an individual expert and in which steps (c)-(j) follow for each expert's decision making structure.

8. The method of claim 1 in which the situation is a medical condition of a patient, the input parameters are physical conditions of the patient and the output actions are possible treatments in response to the medical condition.

9. The method of claim 8 in which there is provided the further step of comparing the output actions of each decision making structure.

10. The method of claim 1 in which step (g) includes generating a biased random value by establishing chi square significance.

11. The method of claim 10 in which there is provided the further step of generating a table of Bayesian probabilities to predict the response for any subsequent situation based on the responses in step (e).

12. The method of claim 11 in which there is provided a further step of interrogating the decision making structure by entering a situation to be analyzed, predicting which path the expert would take through the decision making structure and determining the probability of the expert's response at each node in the decision making structure to arrive at an output action.

13. The method of claim 12 in which there is provided the further step of determining for each group of output actions the probability of selection by the expert of those output actions.

14. A method for selecting from a set of output actions, designated by an expert, for combinatory situations defined by a plurality of input parameters having input values which define a case situation comprising the steps of:

(a) establishing a decision making structure having a plurality of linked nodes extending from a first node and ending in a terminal node with each node defining a question;

(b) entering the input values of the input parameters defining a case situation to be analyzed;

(c) determining which input values of the case situation are significant from node to node and predicting which responses the expert would make for the question posed at the first node based on the values of the significant parameters and then predicting the response for the questions posed at each subsequent node, said subsequent nodes forming a path based on the previous responses through the decision making structure;

(d) repeating step (c) through the linkages of the nodes until a predicted response is an output action at a terminal node of the decision-making structure; and (e) determining the probability that the expert would have selected the output action predicted in step (d).

15. The method of claim 14 in which step (d) further includes determining at a terminal node for all output actions the probability of selection by the expert of each output action from the set of output actions.

16. The method of claim 14 in which steps (b) and (c) include generating the probability that a given path through the linked nodes of the decision-making structure would be chosen by the expert in determining the selection of the output action.

17. A system for selecting from a set of output actions, designated by an expert, for combinatory situations defined by a plurality of input parameters having input values which define a case situation, comprising means for establishing a decision making structure having a plurality of linked nodes extending from a first node and ending in a terminal node with each node defining a question;

means for entering input values of the input parameters defining a case situation to be analyzed;

means for determining which input values of the case situation are significant from node to node and means for predicting which responses the expert would make for the question posed at the first node based on the values of the significant parameters;

means for predicting the response for the questions posed at each subsequent node, said subsequent nodes forming a path based on the previous responses through the decision making structure;

means for determining which input values of the case situation are significant from node to node and predicting which responses the expert would make for the question posed at each of the nodes subsequent to said first node based on the values of the significant parameters until a predicted response is an output action at a terminal node of the decision making structure;

means for determining the probability that the expert would have selected the output action predicted.

18. The system of claim 17 in which there is further provided means for interrogating the decision making structure by entering a situation to be analyzed;

means for predicting which path the expert would take through the decision making structure; and, means for determining the probability of the expert's response at each node in the decision making structure to arrive at an output action.

* * * * *